United States Patent [19]

Weiler et al.

[11] Patent Number: 5,121,856

[45] Date of Patent: Jun. 16, 1992

[54] SLEEVED DISPENSING VIAL

[75] Inventors: Gerhard H. Weiler, South Barrington; Henry Komendowski, Des Plains, both of Ill.

[73] Assignee: Automatic Liquid Packaging, Inc., Woodstock, Ill.

[21] Appl. No.: 620,273

[22] Filed: Nov. 30, 1990

[51] Int. Cl.⁵ .............................................. B65D 37/00
[52] U.S. Cl. .................................. 222/209; 222/215; 222/541; 604/192
[58] Field of Search ................ 222/541, 209, 92, 107, 222/183, 215; 604/192, 200, 212, 256, 263

[56] References Cited

U.S. PATENT DOCUMENTS

| | | | |
|---|---|---|---|
| 208,273 | 9/1878 | Stewart | 222/183 |
| 2,134,489 | 10/1938 | Scherer | 222/107 |
| 2,869,545 | 1/1959 | Forsyth | 604/192 |
| 3,124,171 | 3/1964 | Mitchell | 222/209 |
| 3,215,142 | 11/1965 | Buono | 222/209 |
| 3,233,785 | 2/1966 | Burke | 222/209 |
| 3,777,949 | 12/1973 | Chiquiari-Arias | 222/541 |
| 3,834,241 | 9/1974 | Garren et al. | 222/209 X |
| 4,248,227 | 2/1981 | Thomas | 222/541 X |
| 4,453,935 | 6/1984 | Newton | 604/263 X |
| 4,752,288 | 6/1988 | Hussey | 604/200 X |

FOREIGN PATENT DOCUMENTS

| | | | |
|---|---|---|---|
| 1248883 | 11/1960 | France | 604/212 |
| 866339 | 4/1961 | United Kingdom | 222/215 |
| 902736 | 8/1962 | United Kingdom | 222/107 |
| 2220354 | 1/1990 | United Kingdom | 604/263 |

Primary Examiner—Michael S. Huppert
Assistant Examiner—Anthoula Pomrening
Attorney, Agent, or Firm—Dressler, Goldsmith, Shore, Sutker & Milnamow, Ltd.

[57] ABSTRACT

A hermetically sealed package is provided that is suitable for dispensing a material into a body cavity. The package includes a container having a dispensing nozzle surrounded by a seamless sleeve that prevents contact between the container's dispensing orifice and body tissue without impeding material flow from the container. Preferably the nozzle is provided with a twist-off closure constituted by a cap joined to the dispensing nozzle by a frangible web that surrounds the dispensing orifice.

18 Claims, 2 Drawing Sheets

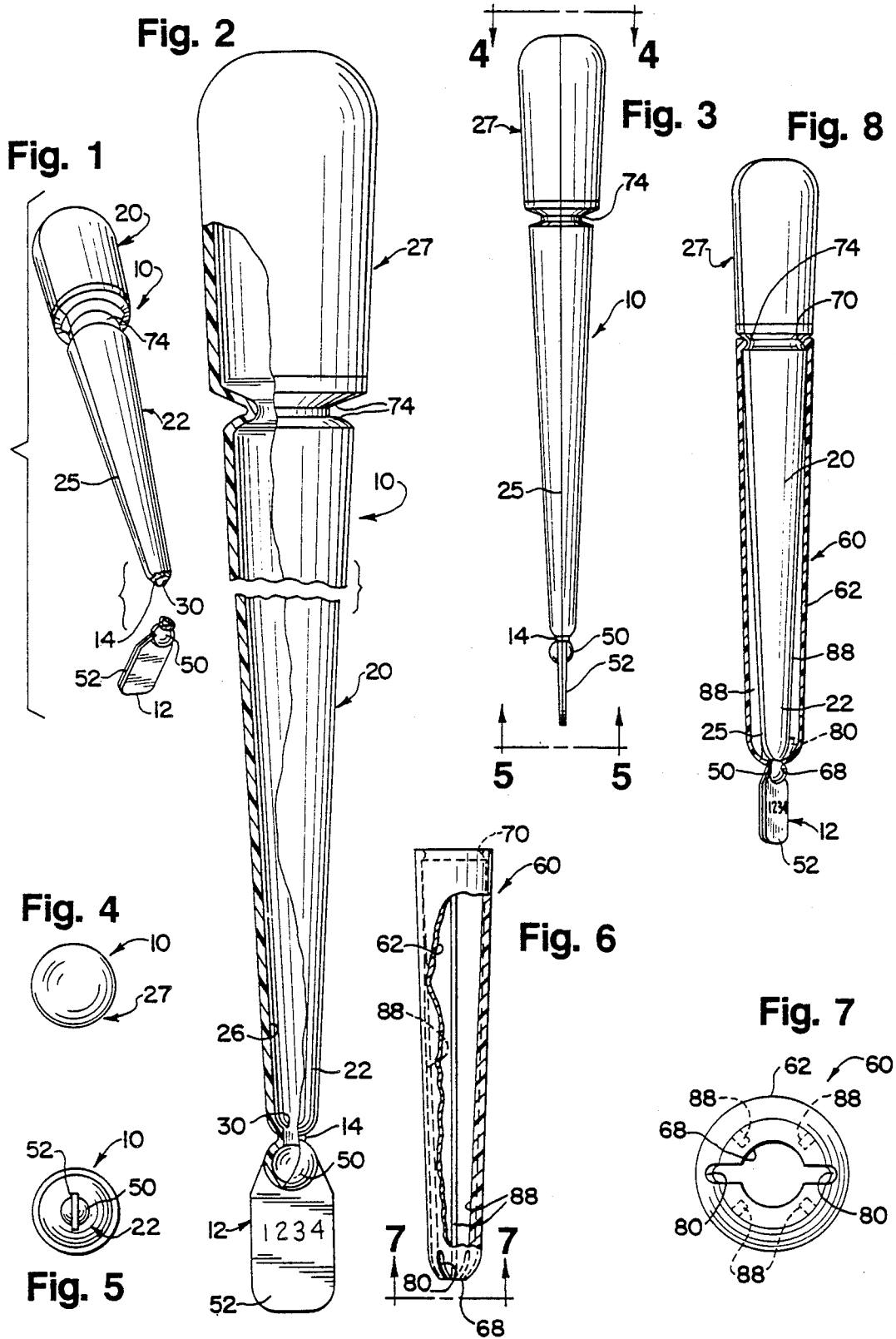

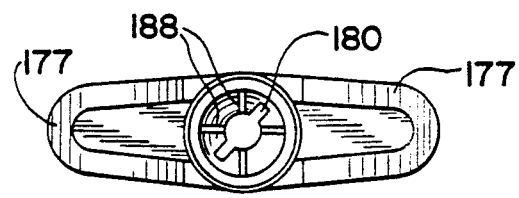
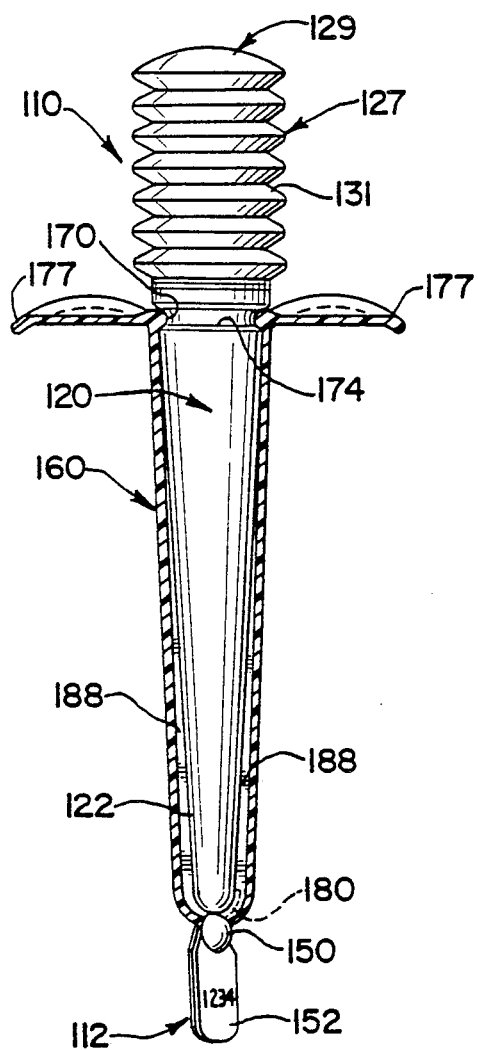
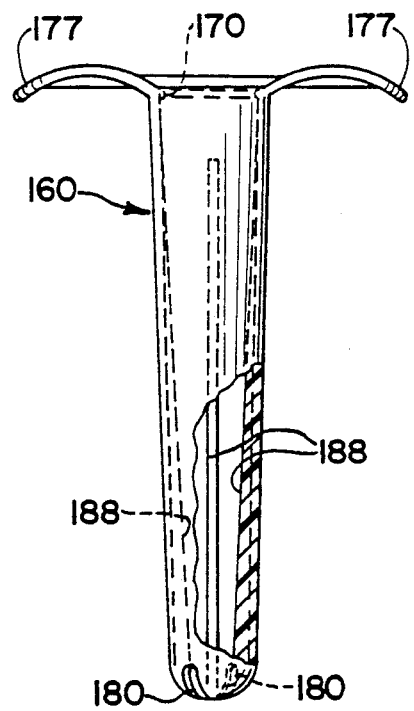

SLEEVED DISPENSING VIAL

TECHNICAL FIELD

This invention relates to a package for dispensing the package contents onto body tissue or into a body cavity. More particularly, the invention relates to a package which includes a container, such as a vial or ampoule, that is hermetically sealed with a top closure structure connected to the container by means of a frangible web.

BACKGROUND OF THE INVENTION

Hermetically sealed containers with unitary closures are known. Such containers typically have a body portion, a neck portion, and a top or closure structure to close and seal the opening in the neck portion.

It is also known to provide such containers with means for permitting the containers to be opened by breaking off the sealed closure at the top of the container or on the neck portion of the container between the container sealed top and the container body portion.

To facilitate the opening of such a container, a frangible web is typically provided between the container neck portion and the closure structure. The frangible web comprises a reduced thickness region in the wall of the material forming the container. Such a container is opened by twisting or bending a part of the container on one side of the frangible web so as to rupture or sever the reduced thickness region of material at the frangible web.

Containers incorporating the above-described frangible web structure are usually formed from a thermoplastic material such as a polyolefin. Such containers are conventionally fabricated by blow molding and/or vacuum forming in split mold parts that close along a parting plane. The formed container typically has a ridge or seam of material on the exterior surface along the parting plane.

The frangible web can be formed in the container neck by conventional techniques during the container molding processes. Of course, before the top closure is molded on the container, the container is filled with the desired contents from a filling nozzle. A typical "formed, filled, and sealed" container of this type is disclosed in U.S. Pat. No. 4,671,763. This patent also discloses the fabrication process as well as the apparatus therefor.

The above-described hermetically sealed, thermoplastic containers are used to package a variety of materials. Such containers have been found to be especially suitable for use in dispensing sterile fluids, such as pharmaceutical solutions and ointments. While these conventional containers function satisfactorily for the purposes for which they have been designed, it would be desirable if the advantages offered by such hermetically sealed containers could be employed in other applications. Specifically, it would be beneficial to be able to use such a container for dispensing a material into a body cavity.

However, the use of such containers for these purposes is not altogether satisfactory. Many such containers are blow molded or vacuum formed from polypropylene in order to provide the characteristics desired for structural integrity, compatibility with the container contents, ease of molding, etc. The ridge or seam formed during container manufacture at the parting plane of such molded containers is relatively prominent and either cannot be altogether eliminated by the usual molding or post-molding flash removal techniques, or require uneconomical procedures to do so. The ridge or seam that is present can irritate if not damage, sensitive tissues and membranes, however. This is a particular problem with respect to applications wherein the user wishes to insert the dispensing end of the container into a body cavity for dispensing the container contents directly into the cavity. For example, this problem militates against the use of a hermetically sealed, blow-molded (or vacuum formed), polypropylene dispensing container for dispensing vaginal lubricants and the like directly into the vagina.

Further, when the closure is removed from the container by tearing or twisting the closure along the connecting frangible web, the exposed dispensing orifice on the container may be surrounded by a relatively rough, uneven, or jagged region which defines the surface at the broken frangible web. This could also irritate or scratch sensitive tissues and membranes.

Although attempts have been made to provide molding processes which reduce both the parting line ridge and the roughness of the broken portion of the frangible web after removal of the closure, such attempts to date have not been completely satisfactory with respect to some intended applications. In view of this, it would be desirable to provide an improved hermetically sealed dispensing package with the convenience of a twist-off closure but without rough edges or portions contacting the body tissues during use.

It would also be advantageous if such an improved package could be relatively small and selfcontained.

Further, it would be beneficial if such an improved package could be readily manufactured by conventional, and relatively inexpensive, processes.

The present invention provides the aforementioned benefits and features.

SUMMARY OF THE INVENTION

The present invention provides a novel package structure for a hermetically sealed, molded thermoplastic container suitable for dispensing material onto body tissue or into a body cavity. The package embodying this invention protects the body tissues from being irritated or injured by the parting plane ridge of the molded material and/or by a rough section of material that could be created when the container is opened by tearing or twisting a closure along a connecting frangible web by providing a seamless sleeve over a dispensing nozzle that is unitary with the body of the container.

The seamless sleeve or shroud is mounted on the container nozzle and has a generally smooth exterior wall that surrounds at least the distal end of the nozzle. The tip or distal end of the sleeve defines an aperture adjacent the dispensing orifice but spaced therefrom. This permits the dispensing of a contained material or substance from the container body after the closure has been removed while contact between body tissue and the container nozzle is prevented. Dispensing of the container contents is aided by a squeezable hollow protuberance that communicates with the container body.

Numerous other advantages and features of the present invention will become readily apparent from the following detailed description of the invention, from the claims, and from the accompanying drawings.

BRIEF DESCRIPTION OF THE DRAWINGS

In the accompanying drawings forming part of the specification, in which like numerals are employed to designate like parts throughout the same, FIG. 1 is a perspective view of a first embodiment of a unitary container having a closure which has been removed from the container nozzle by rupturing a frangible web that normally connects the closure to the container nozzle;

FIG. 2 is a greatly enlarged, front elevational view of the container of FIG. 1 in the unitary condition prior to removal of the closure and shows portions of the structure broken away to better illustrate interior detail;

FIG. 3 is a side elevational view of the container;

FIG. 4 is an end view taken along the plane 4—4 in FIG. 3;

FIG. 5 is an end view taken along the plane 5—5 in FIG. 3;

FIG. 6 is a side elevational view of a sleeve for the container, and the sleeve is shown with portions cut away to better illustrate interior detail;

FIG. 7 is greatly enlarged end view taken along the plane 7—7 in FIG. 6;

FIG. 8 is a view similar to FIG. 3 but with the container rotated slightly and with the sleeve assembled on the container to form a complete dispensing package;

FIG. 9 is a front elevational view of a second embodiment of the package of the present invention which embodiment includes a bellows-type squeeze bulb and finger rests on the container sleeve;

FIG. 10 is a side elevational view of the sleeve on the package shown in FIG. 9 but with portions cut away to show interior detail; and FIG. 11 is a plan view of the sleeve shown in FIG. 10.

DESCRIPTION OF THE PREFERRED EMBODIMENTS

While this invention is susceptible of embodiment in many different forms, this specification and the accompanying drawings disclose only some specific forms as examples of the invention. The invention is not intended to be limited to the embodiments so described, and the scope of the invention will be pointed out in the appended claims.

For ease of description, the package of this invention is described in the normal (inverted) dispensing position, and terms such as upper, lower, horizontal, etc., are used with reference to this position. It will be understood, however, that the package of this invention may be stored, transported, used, and sold in an orientation other than the position described. The container included in this package is manufactured by the form-fill-seal technique in the position shown in FIG. 2.

The package of this invention may be fabricated and assembled with conventional molding apparatus and other mechanisms, the details of which, although not fully illustrated or described, will be apparent to those having skill in the art and an understanding of the necessary functions of such apparatus and mechanisms. The detailed descriptions of such apparatus or other mechanisms are not necessary to an understanding of the invention and are not herein presented because such apparatus and other mechanisms form no part of the present invention.

The present invention permits a variety of thermoplastic materials, preferably low density polyethylene, to be molded with a split molding process to provide a hermetically sealed dispensing package which can be opened by rupturing a frangible web around a dispensing orifice and used to dispense medication and the like substances into a body cavity. The present invention provides a means for preventing the body tissues from contacting the parting plane ridge and/or the rough surface of the opened container dispensing end that may be present. Thus, the dispensing package can be used to dispense materials directly into a body cavity or against body tissue.

A first type of a container which is part of the package embodying the present invention is illustrated in FIGS. 1 and 8. The container is designated generally by the reference numeral 10 (FIG. 1) and the sleeve by reference numeral 60 (FIG. 8). In FIG. 1 the container 10 is shown with sleeve 60 removed and having been opened by breaking away a closure 12 from the rest of the container at a frangible connecting region or web 14.

The container 10 is initially molded and filled as a unitary, hermetically sealed structure (FIGS. 2-5) generally utilizing the technique and apparatus described in U.S. Pat. No. 4,671,763 to Weiler et al.; however, the container is made in the position shown in FIG. 2, so that the web 14 is formed by the main mold parts and the seal mold parts shape the upper portion of the container after filling.

The container 10 includes an elongated hollow body portion 20 and a dispensing nozzle or neck 22 that is unitary with, and extends from one end of the body 20. Nozzle 22 defines a dispensing passage 26 communicating with the interior of the body 20. The nozzle 22, and thus passage 26, terminate at a distal end that defines dispensing orifice 30, initially occluded by the closure 12. Web 14 connects closure 12 to the nozzle 22. For a twist-off closure, web 14 is made thin enough to be frangible. In the alternative, web 14 can be relatively thicker and can be severed with a knife, scissors, or like implement.

The closure 12 includes a plug such as the generally spherical occlusion or closure portion 50 and a graspable oblate tab 52. The spherical closure portion 50 seals the nozzle 22 across the orifice 30 at the web 14. The interior of the closure portion 50 preferably includes a hollow, concave configuration that is open to the dispensing passage 26.

The web 14, preferably frangible, is formed in an annular configuration during molding as a unitary part of the container 10 and circumscribes the junction between the container nozzle 22 and the closure portion 50. The frangible web 14 defines a locus of potential fracture at which the separation of the closure 12 from the container nozzle 22 occurs when the container 10 is opened in a manner as is next described in detail. On the container interior, adjacent to web 14, there is a smooth, cylindrical wall portion that is wider than the web 14. To be frangible, the web 14 typically has a thickness that is considerably less than the wall thickness on either side of the web.

To open the container 10, the container 10 is grasped in one hand about the nozzle 22, and the tab 52 is grasped between the thumb and forefinger of the other hand. Next, the tab 52 is twisted or bent relative to the container nozzle 22 to cause separation of the closure 12 from the container nozzle 22 at the web 14. This causes the web connection to rupture. Preferably, the closure 12 and at least portion of the nozzle 22 are relatively rigid so that manipulation of the closure 12 causes the fracture or rupture of the frangible web and a complete separation of the closure 12 from the container nozzle 22.

The frangible web 14 may have any conventional configuration suitable for grasping and manipulation. The detailed design of the frangible web structure forms no part of the present invention.

The container 10 may be fabricated by conventional blow-molding processes and apparatuses from suitable thermoplastic material, usually low-density polyethylene, or the like. Typically, the container is blow-molded and then filled in a mold assembly that includes two, coacting, main mold halves to mold the container body 20, the nozzle 22, the frangible web 14, and the closure 12. The upper portion of the container, including a squeezable hollow protuberance such as squeezable bulb means 27, is formed by a pair of coacting sealing mold halves. Alternatively, the frangible web 14 may be formed against a mandrel inserted in the orifice 30 or may be formed by other suitable conventional processes.

After the container is blow-molded in the main mold halves and filled with a desired substance via a filling assembly, the sealing mold halves are closed to complete the molding of the container upper portion and hermetically seal the contents in the container. Such a container molding process, or other suitable variations of it, are well-known and form no part of the present invention.

In the preferred embodiment of the invention illustrated in FIGS. 1-5 and 8, a portion of the container 10 may have a wall thickness and configuration that permits the container, or portions thereof, to be squeezed so as to dispense the container contents through the nozzle 22 after the container has been opened as described above. To this end, in some applications, it may be desirable to entrap in the container 10 some amount of air or an inert gas in addition to the material or materials which are to be dispensed from the container 10. To further facilitate dispensing of the container contents, a squeezable hollow protuberance such as hollow bulb 27 is provided for container 10 at the end of container body portion 20 opposite that terminating in nozzle 22. The hollow bulb can have various configurations.

In one contemplated application, the container 10 may be filled with a relatively viscous pharmaceutical preparation such as a vaginal lubricant. When used in such an application, it is obviously desirable that the container 10 not unduly irritate the mucous membranes that it may contact during dispensing.

However, if the dispensing container 10 is formed in a split mold from a thermoplastic material, then the container exterior usually will have a ridge or seam along the parting plane. This can be especially troublesome where the container 10 is fabricated from polyethylene material by conventional, blow-molding techniques employing two mold halves which close about a parting plane. The thermoplastic material tends to form a small upset ridge 25 on the parting plane, and this may result in a somewhat sharp or rough configuration along the entire length of the container nozzle 22 (as well as along the container body 20).

Further, when the container is opened by rupturing the frangible web, a sharp, jagged, or rough surface or burr may be created at the ruptured frangible web. When such an opened container 10 is held against the skin or inserted into a body cavity, there may be some irritation of the body tissues where the parting plane ridge material 25 and/or ruptured frangible web 14 may come in contact with tissues.

The package of the present invention provides a novel structure which prevents the parting plane ridge of material 25 and/or rough surfaces of the broken web 14 around the opened dispensing orifice 30 from contacting the body tissues. Specifically, a unique, seamless shroud or sleeve 60 (FIGS. 6-8) is provided on the container 10 and envelops at least the distal end of nozzle 22. The sleeve 60 has a smooth, seamless exterior wall 62. In the embodiment illustrated in FIGS. 6-8, the seamless wall 62 of sleeve 60 projects beyond the web 14, but stops short of tab 52 and defines an aperture 68 which is in substantial registry with, and is axially spaced from the web 14 as well as orifice 30 so as to prevent contact of body tissues by the nozzle 22.

The proximal end portion or base of the sleeve 60 includes an inwardly directed, annular rib 70 for engaging annular channel or groove 74 in the container 10. Preferably annular channel 74 is situated between the container body 20 and the hollow, squeezable bulb 27 and receives the sleeve rib 70 in a snap-fit engagement as illustrated in FIG. 8. Alternatively, seamless sleeve 60 can be secured onto the container nozzle by a bayonet lock, by gluing, or by similar expedients.

In order to accommodate assembly of the sleeve 60 over tab 52 and onto the container 10, the distal end portion of the sleeve 60 defines a pair of opposed slots or channels 80 at the aperture 68. In this manner the closure tab 52 is accommodated as the sleeve 60 is moved axially onto the nozzle 22 and into the fully engaged position (as illustrated in FIG. 8).

The distal end of the sleeve 60 curves inwardly and preferably is sufficiently resilient around the aperture 68 to accommodate some outward deformation. Depending upon the relative dimensions, this may be necessary to enable the aperture 68 to move past the spherical closure portion 50 in instances when it has a diameter slightly larger than the diameter of the aperture 68. When the sleeve 60 is in the fully seated or engaged position on the container 10 (FIG. 8), there still may be a slight outward deformation of the distal end of the sleeve 60 so that it is in tight engagement with the surface of the spherical closure portion 50.

In the embodiment illustrated in FIGS. 1-5 and 8, wherein the container nozzle 22 tapers radially inwardly toward the distal end, the sleeve 60 is preferably provided with a plurality of internal ribs 88 that are complementary to the exterior surface of the container nozzle 22, function to align the sleeve 60 with the nozzle 22 and also provide rigidity to the sleeve and the overall assembly.

When the closure 12 is removed, the closure spherical portion 50 becomes disengaged from the distal end of the sleeve 60. Thus, the diameter of the aperture 68 may decrease slightly as the tip or distal end of sleeve 60 returns to an unstressed configuration.

The sleeve 60 provides a smooth, seamless surface for eventual contact with body tissues while the contents of container 10 is dispensed. Both the sleeve aperture 68 (through which the container contents are discharged) and the exterior surface of the sleeve are smooth and non-abrasive to the touch.

A smooth exterior surface for sleeve 60 can be easily effected by injection molding. By contouring sleeve 60 with a slight draft or taper, a molded sleeve can be easily withdrawn from an injection mold cavity.

Further, since the tip or distal end of the sleeve 60 usually projects beyond the residue from frangible web 14 when the container 10 is opened by rupturing the frangible web, the sleeve aperture 68 is spaced from the dispensing orifice and any resulting sharp or rough edges surrounding the dispensing orifice are necessarily recessed inwardly of the tip of the sleeve 60. Preferably, the dispensing orifice is recessed about 1/16 to about ⅛ of an inch from the sleeve aperture. Thus, the likelihood of tissue contact with the container nozzle 22 is substantially reduced, if not altogether eliminated.

A second embodiment of the package of the present invention, provided with a bellows-type bulb means to assist dispensing, is illustrated in FIGS. 9-11.

In this particular embodiment, parts performing a function similar to that in the embodiment illustrated in FIGS. 1-8 are identified by 100-series numbers having the same last two digits. Thus, in FIG. 9 container 110 is shown having container body portion 120 a well as tapered dispensing nozzle 122 enveloped in a prolate seamless sleeve 160. Squeezable hollow protuberance 127 is provided at the end of container body 120 opposite dispensing nozzle 122 in the form of a bellows-type cylinder 129 that is collapsible substantially along the longitudinal axis of elongated container body 120. Specifically, bellows-type cylinder 129 is formed unitary with body portion 120 and with circumferential, flexible pleats 121 that permit collapse of the cylinder 129 upon application of a compressive force along the longitudinal dimension of the cylinder.

Seamless sleeve 160 is mounted to container 110 by means of inwardly projecting bead or flange 170 that is received into circumferential groove 174 molded in body portion 120. To facilitate the application of a compressive force to the bulb 127, seamless sleeve 160 also has unitary finger rests, such as the curved opposed finger rests 177 at the proximal end.

As can be seen from FIGS. 10 and 11, seamless sleeve 160 also has plural longitudinal internal ribs 188 spaced from one another about the inner surface of wall 162. While four longitudinal ribs 188 spaced about 90 degrees apart are shown in FIG. 11, three such ribs spaced about 120 degrees apart, or even two such ribs spaced about 180 degrees apart can be utilized.

Opposed slots 180 at the tip or proximal end of seamless sleeve 160 extend radially outwardly from sleeve aperture 168 to accommodate the tab 152 of closure 112 during package assembly.

The package of the present invention permits the use of blow-molded containers for dispensing materials into body cavities notwithstanding the presence of a parting line on such a container. The present novel package prevents substantial contact between body tissues and a protruding parting line and/or rough dispensing orifice of a blow-molded container. The present improved package can be readily fabricated in a single dose, self-contained configuration by conventional, and relatively inexpensive, processes.

It will be readily apparent from the foregoing detailed description of the invention and the illustrated embodiments thereof that numerous other variations and modifications may be effected without departing from the true spirit and scope of the novel concepts or principles of this invention.

We claim:

1. A hermetically sealed, molded package suitable for dispensing a substance into a body cavity, said package comprising:

an elongated container body terminating at one end in a unitary dispensing nozzle and in a squeezable hollow protuberance at the other end; said nozzle defining a dispensing orifice occluded by a unitary closure at the distal end of the nozzle;

a frangible web sealingly connecting said closure to said nozzle around said dispensing orifice while permitting removal of said closure upon rupturing of said web; and a seamless sleeve mounted on said container body about said nozzle and surrounding the dispensing orifice and at least the distal end of said nozzle but not said unitary closure; said sleeve including a plurality of ribs circumferentially spaced about the interior of said sleeve and the distal end portion of said sleeve defining an aperture for dispensing of the package contents after said closure has been removed.

2. The package in accordance with claim 1 in which said dispensing nozzle is tapered toward said dispensing orifice.

3. The package in accordance with claim 1 in which each said rib is sized along its length so as to contact said dispensing nozzle when said sleeve is mounted on said container body.

4. The package in accordance with claim 1 in which said sleeve curves inwardly at the distal end portion thereof to define said aperture.

5. The package in accordance with claim 4 in which said sleeve at the distal end portion thereof also defines a pair of opposed slots that each open to said aperture to allow passage of said closure through said aperture.

6. The package in accordance with claim 1 in which said sleeve includes an annular bead for snap-fit engagement with said container body.

7. The package in accordance with claim 1 in which said hollow protuberance is a compressible, unitary bulb means that communicates with the container body.

8. A hermetically sealed package suitable for dispensing a contained material into a body cavity, said package comprising:

a container body having a dispensing nozzle sized for insertion into a body cavity, said nozzle defining a dispensing orifice occluded by a removable unitary closure;

a web sealingly connecting said closure to said nozzle at said dispensing orifice;

a squeezable hollow protuberance in communication with the container body; and a sleeve mounted on said container body and defining a seamless exterior surface surrounding at least the distal end portion of said nozzle, said sleeve including a plurality of ribs circumferentially spaced about the sleeve interior and said nozzle said sleeve extending beyond said dispensing orifice and defining an aperture substantially in registry with said dispensing orifice but spaced from said dispensing orifice; whereby said sleeve prevents contact between body tissue and said dispensing orifice.

9. The package in accordance with claim 8 in which said nozzle is tapered toward the dispensing orifice and in which said orifice is circular.

10. The package in accordance with claim 8 in which said sleeve tapers inwardly toward the distal end portion thereof.

11. The package in accordance with claim 8 in which said sleeve is an injection-molded sleeve.

12. The package in accordance with claim 8 in which material of construction of said container body is low-density polyethylene.

13. The package in accordance with claim 8 in which said hollow protuberance is a compressible, unitary bulb means delineated by an annular channel about said container body and in which said sleeve defines an annular bead for snap-fit engagement with said annular channel.

14. The package in accordance with claim 8 wherein said sleeve aperture is spaced from said dispensing orifice.

15. The package in accordance with claim 8 wherein said sleeve is provided with finger rests at the proximal end of the sleeve.

16. The package in accordance with claim 8 wherein said sleeve has a prolate form, said nozzle is tapered toward the dispensing orifice, and said sleeve envelops the container body as well as the nozzle.

17. The package in accordance with claim 8 wherein said hollow protuberance is a compressible bulb unitary with the container body and at the end thereof opposite said nozzle.

18. The package in accordance with claim 8 wherein said hollow protuberance is a compressible bellows cylinder unitary with the container body and at the end thereof opposite said nozzle.

* * * * *